United States Patent [19]
Lyons et al.

[11] Patent Number: 5,898,029
[45] Date of Patent: Apr. 27, 1999

[54] DIRECT INFLUENCES ON NERVE GROWTH OF AGENTS THAT INTERACT WITH IMMUNOPHILINS IN COMBINATION WITH NEUROTROPHIC FACTORS

[75] Inventors: W. Ernest Lyons, Columbia; Edwin B. George; Ted M. Dawson, both of Baltimore; Joseph P. Steiner, Hampstead; Solomon H. Snyder, Baltimore, all of Md.

[73] Assignee: The John Hopkins University, Baltimore, Md.

[21] Appl. No.: 08/229,601

[22] Filed: Apr. 12, 1994

[51] Int. Cl.$^6$ .......................... A61K 38/18; A61K 31/435
[52] U.S. Cl. .................................. 514/12; 514/2; 514/291
[58] Field of Search ................................ 424/600; 514/1, 514/2, 9, 11, 291, 12; 11/11

[56] References Cited

U.S. PATENT DOCUMENTS

| | | |
|---|---|---|
| 5,100,899 | 3/1992 | Calne . |
| 5,330,993 | 7/1994 | Armistead et al. . |
| 5,614,547 | 3/1997 | Hamilton et al. . |

FOREIGN PATENT DOCUMENTS

| | | |
|---|---|---|
| 0184162 | 6/1986 | European Pat. Off. . |
| 2279006 | 12/1994 | United Kingdom . |

OTHER PUBLICATIONS

Gold et al., "An Immunosuppressant Increases Funcitonal Recovery and Axonal Regeneration in the Rat Following Axotomy of the Sciatic Nerve", *Society for Neuroscience Abstracts*, 19:543.18 (1993).

Steiner et al., "The Immunosuppressant FK–506 Enhances Phosphorylation of GAP63: Implications for a Role in Modulation of Growth Cone Function and Neurotransmiter Release", *Society for Neuroscience Abstracts*, 18:262.8 (1992).

Steiner et al., "Increased Expression of FK–506 Binding Protein During Peripheral Nerve Regeneration", *Society of Neuroscience Abstracts*, 18:262.7 (1992).

Lyons et al., "Immunosuppressant FK506 Promotes Neurite Outgrowth in Cultures of PC12 Cells and Sensory Ganglia", *Proc. Natl. Acad. Sci. USA*, 91:to be released (1994).

Rajoofetra et al., *Brain Research*, vol. 572, pp. 329–334, 1992.

Tindall, *J. Autoimmunity*, vol. 5 (Suppl. A) pp. 301–313, 1992.

Lopez et al., *Transplant. Proceed.*, vol. 23, pp. 3181–3182, 1991.

Jackowski, *Br. J. Neurosurgery*, vol. 9, pp. 303–317, 1995.

Stoltenburg–Didinger et al. Neurotoxicology 13:179–184 (1992).

Appel et al. Arch. Neurol. 45 381–386 (1988).

Longo et al. in *Neurotrophic Factors*. Loughin et al, eds. (Acad. Press. 1993) pp. 235–237.

Lindsay et al. 1*bid.*, pp. 265–267.

*Primary Examiner*—Paula K. Hutzell
*Assistant Examiner*—Stephen Gucker
*Attorney, Agent, or Firm*—Banner & Witcoff, Ltd.

[57] ABSTRACT

Immunophilin ligands act by binding to receptor proteins, immunophilins, which in turn can bind to and regulate the $Ca^{2+}$ dependent phosphatase, calcineurin, and the $Ca^{2+}$ release channel, the ryanodine receptor. Immunophilin ligands have been discovered to enhance neurite outgrowth in neuronal cell systems by increasing sensitivity to neurotrophic factors. The effects of the immunophilin ligands are detected at subnanomolar concentrations indicating therapeutic application in diseases involving neural degeneration.

29 Claims, 13 Drawing Sheets

CRUSH
FIG. 2A A
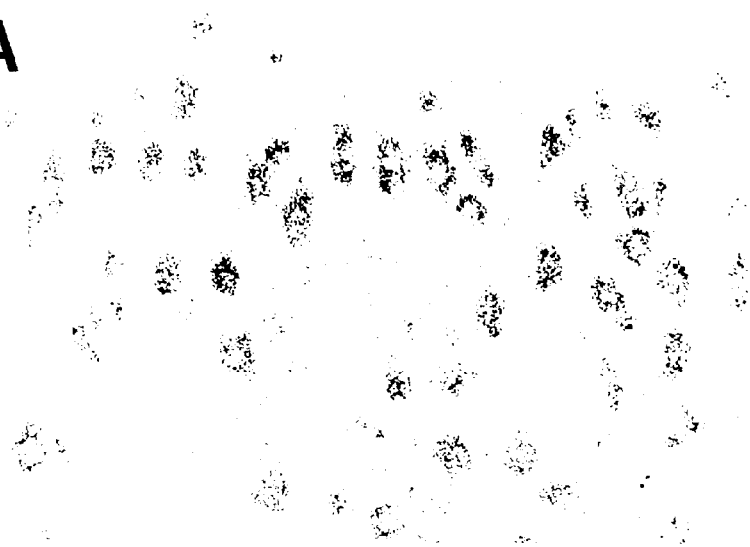
FIG. 2B B
CONTROL

FIG. 3A
LUMBAR SPINAL CORD
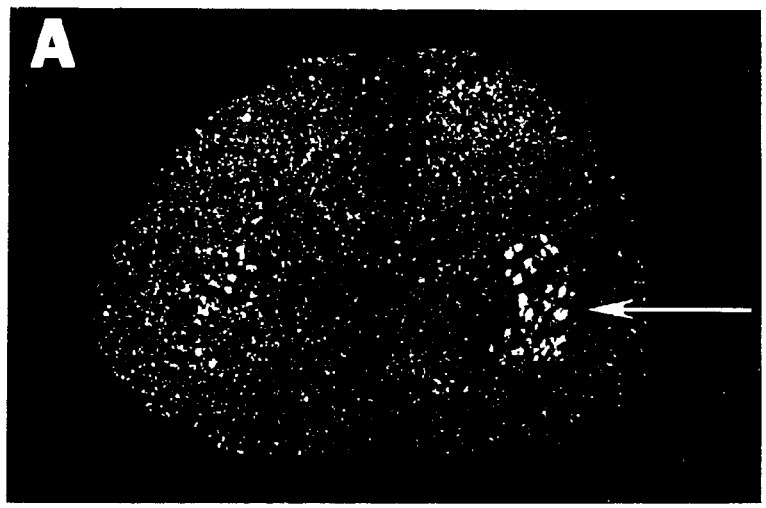
CONTROL          CRUSH
FIG. 3B          FIG. 3C

FIG. 5

RICIN LESION

FKBP

NISSL

FIG. 9
| NGF 1ng/ml | NGF 50ng/ml |
|---|---|
| 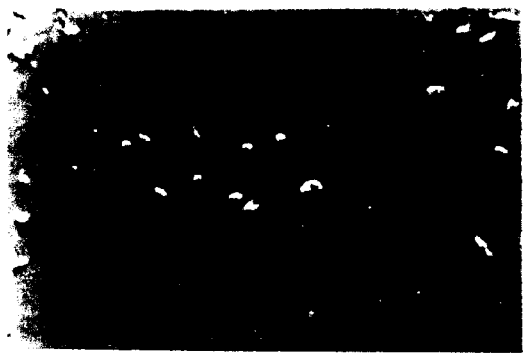 |  |
|  |  |
| NGF 1 ng/ml<br>FK506 0.1 μM | NGF 1 ng/ml<br>RAPA 0.1μM |

[3H] FK506

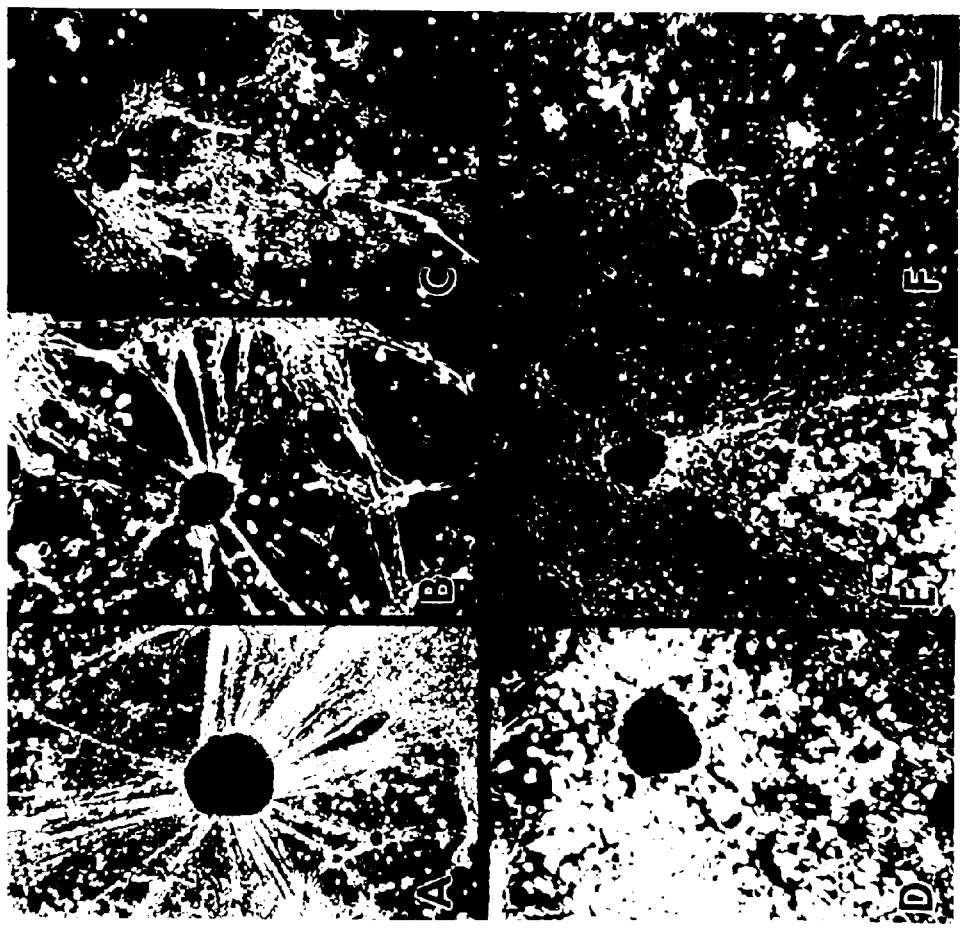

DIRECT INFLUENCES ON NERVE GROWTH OF AGENTS THAT INTERACT WITH IMMUNOPHILINS IN COMBINATION WITH NEUROTROPHIC FACTORS

This invention was made under USPHS grants MH-18501, DA00266, and DA00074. The U.S. government therefore retains certain rights in the invention.

BACKGROUND OF THE INVENTION

The immunosuppressant drugs cyclosporin A and FK506 are thought to exert their therapeutic effects by binding to receptor proteins, designated cyclophilins and FK506 binding proteins (FKBP) respectively. When complexed to the immunosuppressant drugs, these binding proteins, designated immunophilins, bind to the $Ca^{2+}$ activated phosphatase, calcineurin, to inhibit its activity and increase levels of phosphorylated calcineurin substrate proteins (1–9). Concentrations of the immunophilins are far higher in the brain and peripheral nervous system than in immune tissues, and FKBP is co-localized with calcineurin throughout the brain, suggesting an important functional relationship (4).

We recently showed that cyclosporin A and FK506 block the neurotoxicity elicited by glutamate acting at N-methyl-D-aspartate (NMDA) receptors in cerebral cortical cultures (10). The mechanism for the neuroprotective effects of these drugs appears to be inhibition of calcineurin with an augmentation of phosphorylated levels of nitric oxide synthase (NOS) (10). Since phosphorylation of NOS inhibits its catalytic activity (11), the immunosuppressants effectively reduce nitric oxide (NO) formation, preventing the neurotoxic effects of NMDA in these cultures (12,13).

GAP43 is a prominent protein in neuronal processes associated with neurite extension and is also a major calcineurin substrate (14). Regeneration of damaged facial and sciatic nerves is associated with a marked augmentation of GAP43 mRNA levels (15–18).

There is a need in the art for methods of stimulating neuronal cells growth, especially in the case of nerve damage by physical injury or disease. Stimulation of neuronal growth allows a quicker and more complete recovery of damaged nerves.

SUMMARY OF THE INVENTION

It is an object of the invention to provide a method of stimulating the growth of neuronal cells.

It is another object of the invention to provide a method of stimulating the regeneration of neurons after damage due to physical injury.

It is still another object of the invention to provide a method of stimulating the growth of neurons after damage due to disease.

These and other objects of the invention are provided by one or more embodiments of the invention described below. In one embodiment of the invention a method of stimulating the growth of neurons is provided. The method comprises:

administering to neuronal cells an immunophilin ligand in an amount sufficient to stimulate the growth of said neuronal cells.

In another embodiment of the invention an alternative method of stimulating the growth of neurons is provided. The method comprises:

administering to neuronal cells an immunophilin ligand and a neurotrophic factor.

These and other embodiments of the invention provide the art with methods of using pharmacologically acceptable substances for the regeneration of nerves after damage due to injury or disease.

BRIEF DESCRIPTION OF THE DRAWINGS

FKBP-12 and GAP-43 expression in the facial nucleus after nerve crush. (FIG. 1A) In situ hybridization comparing the time course of expression of mRNA in the facial nucleus for FKBP-12 (left) and GAP-43 (right). The right facial nucleus is ipsilateral to the crush, and the left side is an unoperated control. (FIG. 1B) In situ hybridization for FKBP-12 on an untreated control (left) and for calcineurin Aα, β7 days following facial nerve crush (right).

Figures 1A, 1B:
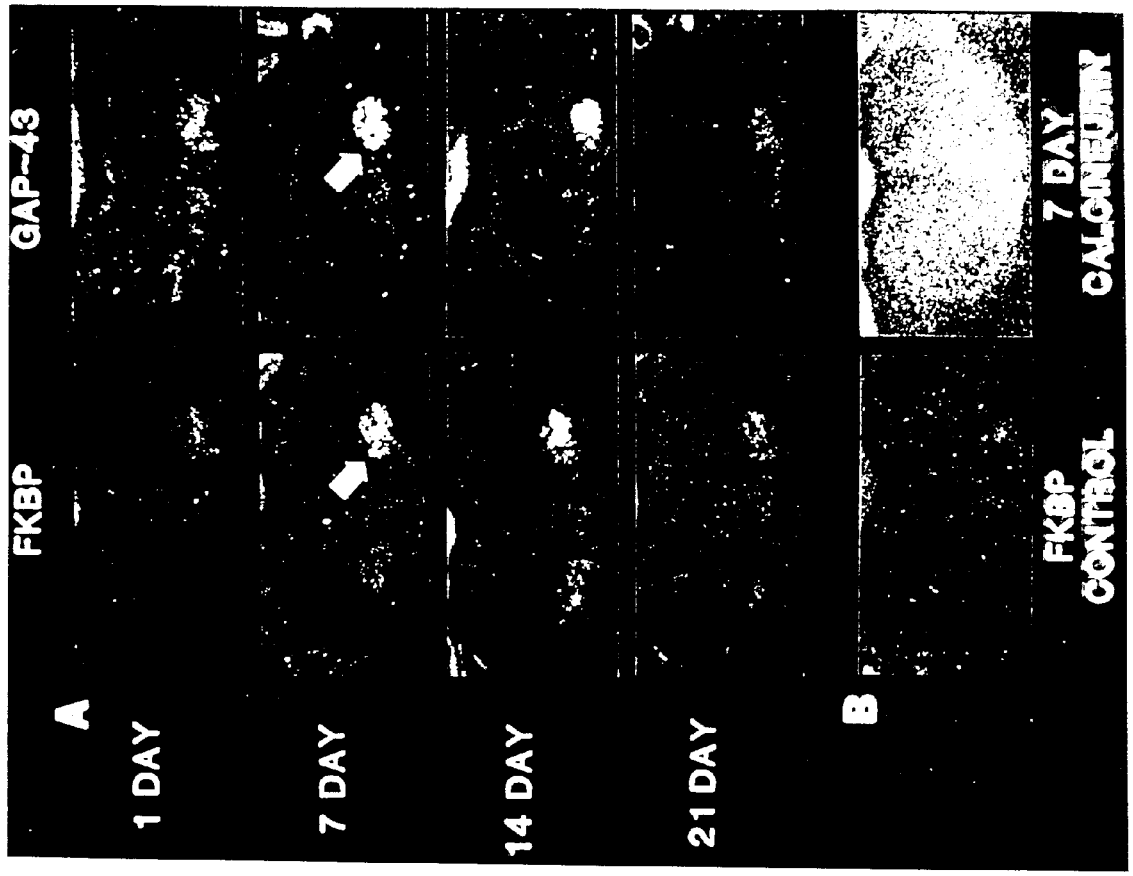
FIGS. 1A and 1B

Experiments were replicated at least 3 times with similar results.

FIGS. 2A and 2B

Localization of FKBP-12 to facial motor neurons following nerve crush. Bright-field photomicrographs of in situ hybridization for FKBP-12 in motor neurons of the facial nucleus 7 days after crush (FIG. 2A), and in motor neurons of control facial nucleus (FIG. 2B).

FIGS. 3A–3C

Upregulation of FKBP-12 mRNA in lumbar spinal cord motor neurons after sciatic nerve crush. In situ hybridization for FKBP-12 7 days after crush of the right sciatic nerve. Top panel (FIG. 3A) shows the response of motor neurons in the ventral horn of lower lumbar spinal cord (indicated by the arrow). Bright field photomicrographs of corresponding motor neuron pools are shown in the bottom panels: (FIG. 3B) left side contralateral to nerve crush, (FIG. 3C) right side ipsilateral to the nerve crush. This experiment was repeated 3 times with similar results.

FIG. 4

Induction of FKBP and FKBP-12 mRNA in the dorsal root ganglion 1 and 6 weeks after sciatic nerve crush. Dark-field photomicrographs of sections through the L4 dorsal root ganglion ipsilateral to sciatic nerve crush processed for FKBP in situ hybridization are shown in the left panels and for [$^3$H]FK506 autoradiography in the right panels. These results were replicated 3 times for each time point.

FIG. 5

Ricin lesion of the right facial nerve. Nissl stain (bottom panel, FIG. 5A) reveals extensive degeneration of motor neurons in the right facial nucleus with an accompanying glial proliferation 7 days following injection of ricin into the facial nerve. In situ hybridization for FKBP mRNA 7 days after ricin lesion of the facial nerve/nucleus is shown in the top panel (FIG. 5B). This experiment was replicated 3 times with similar results.

FIG. 6

[$^3$H]FK-506 binding in segments of sciatic nerve 7 days following crush. The diagram illustrates the 3 mm segments of nerve taken: constrictions indicate positions of ligatures applied at day 7 for the 6 hr collection time as described in the methods. The distal ligature site is 10 mm proximal to the original crush site. Anterograde transport of FKBP is 124 mm/day. Data are the means ±S.E.M. (n=3).

FIGS. 7A–7D

Transport of FKBP in the sciatic nerve. Dark-field photomicrographs of sections through a control (untreated) sciatic nerve and a 7 day sciatic nerve crush site processed for FKBP-12 in situ hybridization (FIG. 7A, FIG. 7B) and for [$^3$H]FK-506 autoradiography (FIG. 7C, FIG. 7D). Arrows indicate the sight of the nerve crush. This experiment was repeated 3 times with similar results.

FIG. 8

Levels of [$^3$H]FK506 binding in PC-12 cells maintained in the presence or absence of NGF (50 ng/ml). n=3 for each time point. Bars represent S.E.M.

FIG. 9

Immunosuppressant mediated enhancement of neurite outgrowth in PC-12 cells. Hoffman contrast photomicrographs (64) of cultures grown for 48 hr in the presence of NGF with or without added FK506 or rapamycin. FIG. 9A: PC-12 cells grown in 1.0 ng/ml NGF. FIG. 9B: 50 ng/ml NGF. FIG. 9C: 1.0 ng/ml NGF and 100 nM FK506. FIG. 9D: 1.0 ng/ml NGF and 100 nM rapamycin. Magnification 200 X.

FIG. 10

Effects of FK506 on neurite outgrowth in PC-12 cells. Cultures were treated with varying concentrations of NGF in the presence or absence or 100 nM FK506, and neurite sprouting was measured at 48 hr. Outgrowth was quantitated as described in Methods by counting cells with neuritic processes greater than 5 μm. n=4 separate experiments for each point and error bars represent SEM.

FIG. 11

Concentration-response relationship for FK506 potentiation of neurite outgrowth in PC-12 cells. Cells were treated for 48 hr with 1 ng/ml NGF and varying concentrations of FK506. Neurite outgrowth response was measured as described in FIG. 10 and Methods. n=4 separate experiments for each data point * p<0.001 Students t test.

FIG. 12

[$^3$H]FK-506 autoradiography on dorsal root ganglion explant cultures. After 26 days of cultures with 100 ng/ml NGF the extensive processes display abundant FKBP associated silver grains. Autoradiographic grains are abolished with 1 μM unlabeled FK506.

FIGS. 13A–13F

Phase-contrast micrographs of dorsal root ganglia grown with different substances. FIG. 13A: NGF 100 ng/ml, FIG. 13B: FK506 1 μM, FIG. 13C: FK506 1 μM and anti-NGF antibody, FIG. 13D: No added growth factor, FIG. 13E: FK506 1 μM, FIG. 13F: FK506 1 μM and rapamycin 1 μM. Scale bar is 250 μm. NGF produces abundant axon outgrowth (FIG. 13A), as does 1 μM FK506 (FIG. 13B). The effects of FK506 are substantially decreased by reducing the concentration to 1 pM (FIG. 13E). However, neurite outgrowth with 1 pM FK506 is greater than in its absence (FIG. 13D). FK506 effects are also diminished by adding anti-NGF antibody to eliminate the effects of NGF produced by non-neuronal cells in the cultures. The abundant neurites that occur in large fascicles in response to NGF (100 ng/ml]) (FIG. 13A) or 1 μM FK506 (FIG. 13B) appear white, while small fascicles or individual neurites appear black. Non-neuronal cells, Schwann cells and some fibroblasts, are more evident with 1 pM FK506 (FIG. 13E) or anti-NGF antibody (FIG. 13C) than with 1 μM FK506 (FIG. 13B). NGF produced by non-neuronal cells in the cultures results in the limited axon outgrowth seen in cultures with no added growth factors (FIG. 13D). The large number of refractile non-neuronal cells, appearing white, tend to overshadow the few neurites (FIG. 13D). Rapamycin completely inhibits axon outgrowth in the presence of FK506 (FIG. 13F) Micrographs are representative of 12–30 ganglia from each experimental condition. Differences between all experimental groups were highly reproducible.

DETAILED DESCRIPTION OF THE PREFERRED EMBODIMENTS

It is a discovery of the present invention that immunophilin ligands have a dramatic effect on nerve cells. This effect is extraordinary in terms of potency, with as little as picomolar amounts of immunophilin ligand being neurotrophic. This effect is, therefore, physiologically relevant.

While not wanting to be bound by any particular theory, it is tempting to speculate that the ligands acting through their respective immunophilins inhibit calcineurin to increase levels of phosphorylated calcineurin substrates. Such a mechanism would fit with findings that neurite outgrowth in several systems is associated with phosphorylation of numerous proteins in the neurite extensions (34, 35).

Immunophilins are specific high-affinity receptors for immunosuppressant drugs. These include cyclophilin and FKBP, which bind to cyclosporin A, and FK-506, respectively. In addition to these compounds, other immunophilin-binding drugs have been developed. Such drugs include rapamycin, FK-520, FK-523, 15-0-DeMe-FK-520, (4R)-[(E)-L-butenyl]-4, N-dimethyl-L-threonine. (6).

The neurotrophic actions of immunophilin ligands have therapeutic ramifications. The extreme potency of FK506 is in the range of neurotrophic proteins. Drugs such as FK506 are readily synthesized and can cross the blood brain barrier. Thus, besides therapeutic effects for neuroprotection in conditions such as stroke (10), FK506 and other small molecules that interact with immunophilins are of use in facilitating neuronal repair. Situations where neuronal repair can be facilitated include, but are not limited to diseases including peripheral nerve damage, whether by physical injury or disease state such as diabetes. In addition, facilitation of neuronal repair is useful for injury or disease states of the central nervous system (spinal cord and brain) including physical damage to the spinal cord, damage to motor neurons such as occurs in amyotrophic lateral sclerosis, brain damage as occurs in strokes, Alzheimer's disease and Parkinson's disease.

The dosage and length of treatment with immunophilin-binding drugs depends on the disease state being treated. The duration of treatment may be a day, a week, or longer, and may, in the case of a chronic progressive illness, such as Alzheimer's disease, last for decades. The immunophilin-binding drugs are administered in a therapeutically effective amount, a typical human dosage of FK-506 ranging from about 0.1 mg/kg of body weight of FK-506 to about 1.0 mg/kg of FK-506, in single or divided doses. The dosage will vary depending on the immunophilin-binding drug to be used and its relative potency. Dosage and length of treatment are readily determinable by the skilled practitioner based on the condition and stage of disease.

Neurotrophic factors, whether endogenously produced or administered, appear to be involved in the mechanism of action of the immunophilin ligands. Such neurotrophic factors can be administered by any means known in the art. Typically, far less neurotrophic factor is required in the presence of an immunophilin ligand to achieve the same effect as in its absence. Suitable neurotrophic factors include, but are not limited to: nerve growth factor, glial derived growth factor, brain derived growth factor, ciliary neurotrophic factor and neurotropin-3.

In therapeutic use, immunophilin-binding drugs can be administered by any route whereby drugs are conventionally administered. Such routes of administration include intraperitoneally, intravenously, intramuscularly, subcutaneously, intrathecally and intraventricularly, as well as orally.

Typical preparations for administration include sterile aqueous or nonaqueous solutions, suspensions and emulsions. Examples of nonaqueous solvents are propylene glycol, polyethylene glycol, vegetable oils such as olive oil and injectable organic esters such as ethyl oleate. Aqueous carriers include water, alcoholic/aqueous solutions and buffered media. Intravenous vehicles include fluid and nutrient replenishers, electrolyte replenishers, such as those based on Ringer's dextrose, and the like. Preservatives and other additives may also be present such as, for example, antimicrobials, anti-oxidants, chelating agents, inert gases, and the like. Oral preparations, such as capsules, tablets, and other forms, can include additives such as cellulose, silica gel and stearic acid.

To be effective therapeutically for central nervous system targets, an immunophilin-binding drug desirably should be able to penetrate the blood-brain barrier when peripherally administrated. However, some immunophilin-binding drugs, like cyclosporin A, do not readily penetrate into the brain. Immunophilin-binding drugs which are unable to penetrate the blood-brain barrier can be effectively administered by, for example, an intraventricular route of delivery. Such drugs can also be used to treat peripheral nerves where penetration of the blood-brain barrier is not an issue.

EXAMPLES

Example 1

This example demonstrates high levels of FKBP in normal peripheral nerve and that these increase following nerve crush.

If FKBP were physiologically associated with neuronal process extension in the actions of GAP-43, then one might anticipate substantial levels of FKBP in peripheral nerve. Accordingly, we measured [$^3$H]FK-506 binding in rat sciatic nerve, as well as in growth cones isolated from 2-day-old rat pups, and compared values with those of the cerebral cortex and several peripheral tissues.

[$^3$H]FK-506 autoradiography was carried out as described (4) on unfixed sections which were thawed and air dried before preincubation for 1 hr in buffer consisting of 50 mM Hepes, 2 mg/ml bovine serum albumin, 5% ethanol, and 0.02% Tween 20 pH 7.4. Sections were then exposed to 1 nM [$^3$H]FK-506 (86.5 Ci/mMol; DuPont-NEN, Boston, Mass.) for 1 hr at room temperature in preincubation buffer. Non-specific binding was defined by addition of 1 μM FK-506. Following incubation, the slides were washed 4×5 min in ice cold preincubation buffer and air dried. The radiolabeled sections were then juxtaposed to tritium-sensitive film or coverslips coated with Kodak NTB-2 emulsion.

TABLE 1

[$^3$H]FK506 BINDING TO SCIATIC NERVE AND GROWTH CONES (A) [$^3$H]FK506 Binding in Sciatic Nerve

| Tissue | Bmax (pmol/mg protein) |
|---|---|
| Adult Rat | |
| Sciatic Nerve | 22.1 |
| Cerebral Cortex | 48.0 |

TABLE 1-continued

[$^3$H]FK506 BINDING TO SCIATIC NERVE AND GROWTH CONES

| Thymus | 9.5 |
|---|---|
| Spleen | 8.0 |
| Neonatal Rat | |
| Forebrain | 25.5 |
| Growth Cones | 10.2 |

B) [$^3$H]FK506 Binding After Sciatic Nerve Crush

| | Bmax fmol/5 mm segment | Bmax pmol/mg protein |
|---|---|---|
| Unoperated | 31.8 ± 2.1 | 21.2 ± 1.4 |
| 7-Day Crush | 136.5 ± 15.7* | 40.1 ± 2.0* |

[$^3$H]FK506 binding was assayed as described in methods. In Table 1A experiments were replicated three times with less than 10% variation. In Table 1B values are presented as the mean ± S.E.M. (n = 3).
*P ≤ 0.05 Students' t-test for independent means.

Of all the tissues examined sciatic nerve binding levels are the highest, somewhat higher than those of the cerebral cortex and about 10× higher than levels in the thymus and spleen, which contain FKBP associated with lymphocytes. See Table 1A.

Evidence for a role of FKBP in nerve regeneration comes from experiments in which we crushed the sciatic nerve of adult rats and 7 days later measured [$^3$H]FKBP binding in a 5 mm segment immediately proximal to the nerve crush.

Sprague-Dawley rats (175–200 g) were anesthetized with a mixture of Rompun (12 mg/kg) Ketamine (30 mg/kg). Using aseptic techniques, the facial nerve was crushed with jewelers forceps 2×30 sec 2 mm distal to its exit from the stylomastoid foramen. Identical procedures were used to crush the sciatic nerve at the level of the mid-thigh.

Results are shown in Table 1B. Total binding in the segment proximal to the crush is quadrupled compared to control values. Since total protein is substantially augmented in the proximal segment, [$^3$H]FK-506 binding per mg protein is only doubled in the proximal segment.

Example 2

This example demonstrates that facial nerve lesions augment the coincident expression of FKBP and GAP-43.

Following crush of the facial nerve, mRNA levels of GAP-43 increase in the facial nerve nucleus (18, 55). Utilizing in situ hybridization, we examined mRNA levels of FKBP, GAP-43 and calcineurin following facial nerve crush.

Rats were perfused transcardially with 150–200 ml ice cold phosphate-buffered saline (PBS) (0.1M, pH 7.4). Tissues were removed and immediately frozen in isopentane (−80° C). Cryostat sections (18 μm thick) were cut and thaw mounted on gelatin coated slides.

In situ hybridization was performed as previously described (4), using antisense oligonucleotide probes end labeled with [$^{35}$S] dATP. For FKBP, three separate oligonucleotides complementary to the following regions of the cloned cDNA (56, 57) were used: 70–114, 214–258, 441–485. For GAP-43, three separate antisense oligonucleotides complementary to nucleotides 961–1008, 1081–1128, 1201–1248 of the cloned CDNA (58) were used. For calcineurin Aα antisense oligonucleotides complementary to the nucleotides 1363–1410 and 1711–1758, (59) and for calcineurin Aβ 1339–1386 and 1569–1616 (60) were used. Sections were thawed and allowed to dry, then fixed for 5 min in 4% freshly depolymerized paraformaldehyde in PBS. Following two rinses in PBS, sections were acetylated with 0.25% acetic anhydride in 0.1 M triethanolamine 0.9% NaCl (pH 8.0), and then dehydrated in graded alcohols, defatted in chloroform for 5 min, rehydrated to 95% ethanol and allowed to air dry. Hybridization was performed overnight at 37° C. in buffer containing 50% deionized formamide, 10% dextran sulfate, 4× SSC, 1× Denhardt's solution, 20 mM phosphate buffer, 0.1 mg/ml salmon sperm DNA, 0.1 mg/ml yeast transfer RNA, 10 mM dithiothreitol, 2.0% betamercaptoethanol (BME), 1.0 mM EDTA and labelled probe (2,000,000 dpm/section). Following hybridization, sections were rinsed in 1× SSC, 1.0% BME for 15 min at room temperature, then twice for 10 min at 55° C., air dried and placed on film or dipped in Kodak NTB-2 emulsion.

Results are shown in FIG. 1A. Striking enhancement of FKBP and GAP-43 expression is observed, while no changes are evident in calcineurin expression. As early as 24 hr following facial nerve crush FKBP expression is increased with peak levels evident at 1–2 weeks, while mRNA concentrations diminish substantially at 3 weeks. Examination under higher magnification reveals that the increased levels of silver grains for FKBP mRNA are confined to neuronal cell bodies (FIG. 2). Northern blot analysis of the dissected facial nucleus confirms the increased levels of FKBP specific mRNA (FIG. 2A). GAP-43 mRNA levels follow a time course closely similar to those of FKBP. By contrast, no changes in calcineurin expression are detected at any of the time points examined (FIG. 1B).

Total cellular RNA from the dissected facial nucleus was isolated. Samples of 10 or 20 ug total RNA were electrophoresed through a 1% agarose, 2.0% formaldehyde gel and transferred to a nylon membrane in 10 nM NaOH. cDNA probes to FKBP labeled with [$^{32P}$]dCTP to a specific activity of 1×10$^9$ cpm/ug by random priming were hybridized overnight at 42° C. in buffer consisting of 50% formamide, 2× SSPE, 7% SDS, 0.5% Blotto and 100 ug/ml salmon sperm DNA. The blots were washed for 20 min at room temperature, and 2×15 min at 65° C. in 0.15× SSC, 0.15% SDS and then exposed to film for 48–96 hrs.

On the unlesioned side a modest increase in silver grains compared to control sections are observed. This is consistent with findings that contralateral neurons also respond to axotomy (61).

Following facial nerve crush, rats develop a facial nerve palsy, which is evident by the lack of whisker movement with functional recovery at 3 weeks coincident with the completion of nerve regeneration (62). In our rats we also observed the loss of whisker movement following nerve crush with a return of function at 3 weeks. Thus, the time course of increased expression of GAP-43 and FKBP correlates with the process of nerve regeneration.

Example 3

This example demonstrates alterations in FKBP and GAP-43 associated with sciatic nerve regeneration.

Figure 4:
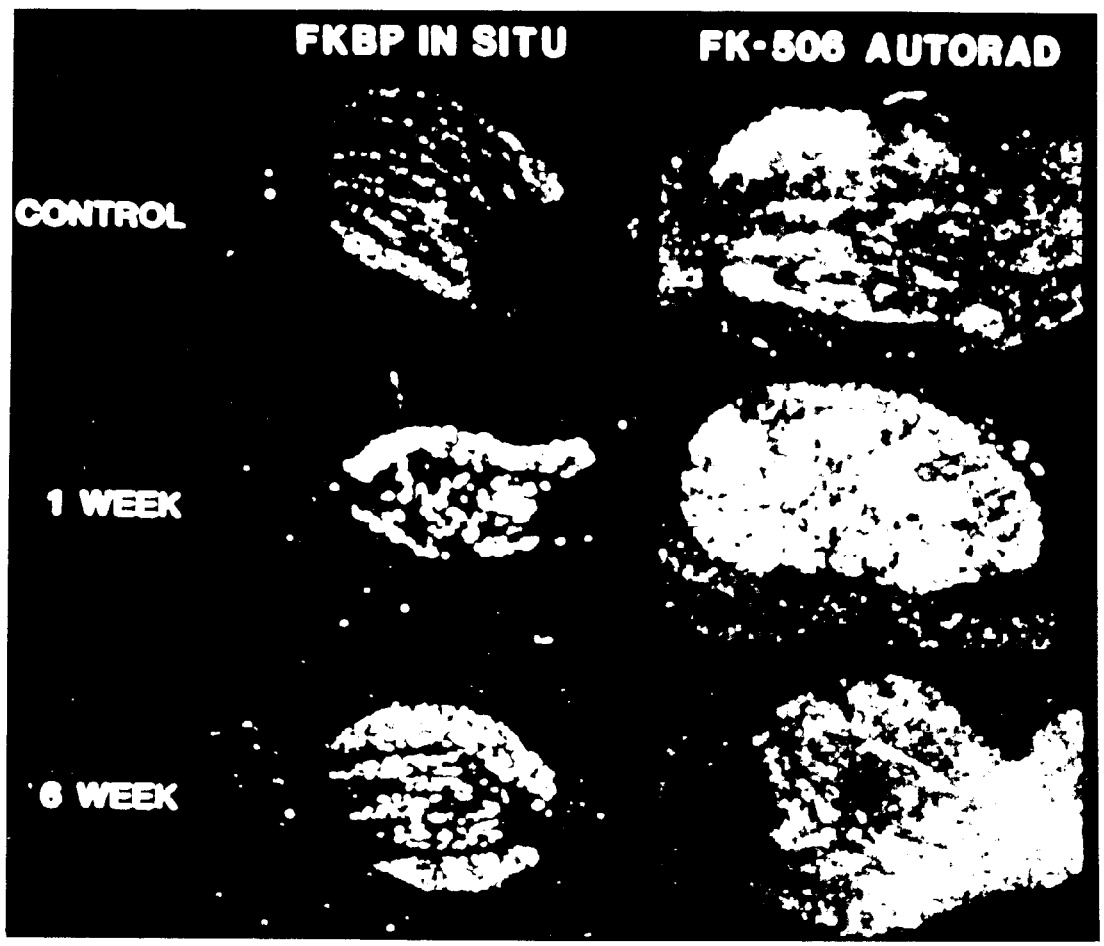

Following sciatic nerve lesions GAP-43 mRNA levels are enhanced in both spinal cord motor neurons and in dorsal root ganglia neuronal cells (63–73). In rats subjected to sciatic nerve crush, we observed a striking enhancement in mRNA levels for FKBP in motor neurons at L-4, 5 (FIG. 3) and in dorsal root ganglia neuronal cells coincident with the reported enhancement of GAP-43 expression (FIG. 4). At high magnification we observed the FKBP mRNA silver grains localized to neuronal cell bodies (FIG. 3). We monitored FKBP protein levels by autoradiography of [$^3$H]FK-506 binding under conditions in which it binds selectively to FKBP (4) (FIG. 4). Increased FKBP is detected in the primary sensory neurons in the dorsal root ganglia, though no increases are evident in motor neuronal cells following sciatic nerve crush.

The association of augmented FKBP expression with regeneration selectively is further supported by experiments with ricin. When injected into peripheral nerves ricin is transported back into the cell body which is destroyed without associated nerve regeneration (74). We injected 0.5 ug ricin (RCA 60, Sigma, St. Louis, Mo.) into the facial nerve at the same site where crushes had been performed in other experiments according to the method of Streit and Kreutzberg in 0.5 ul PBS and 0.1% Fast Green (75).

Figure 5:
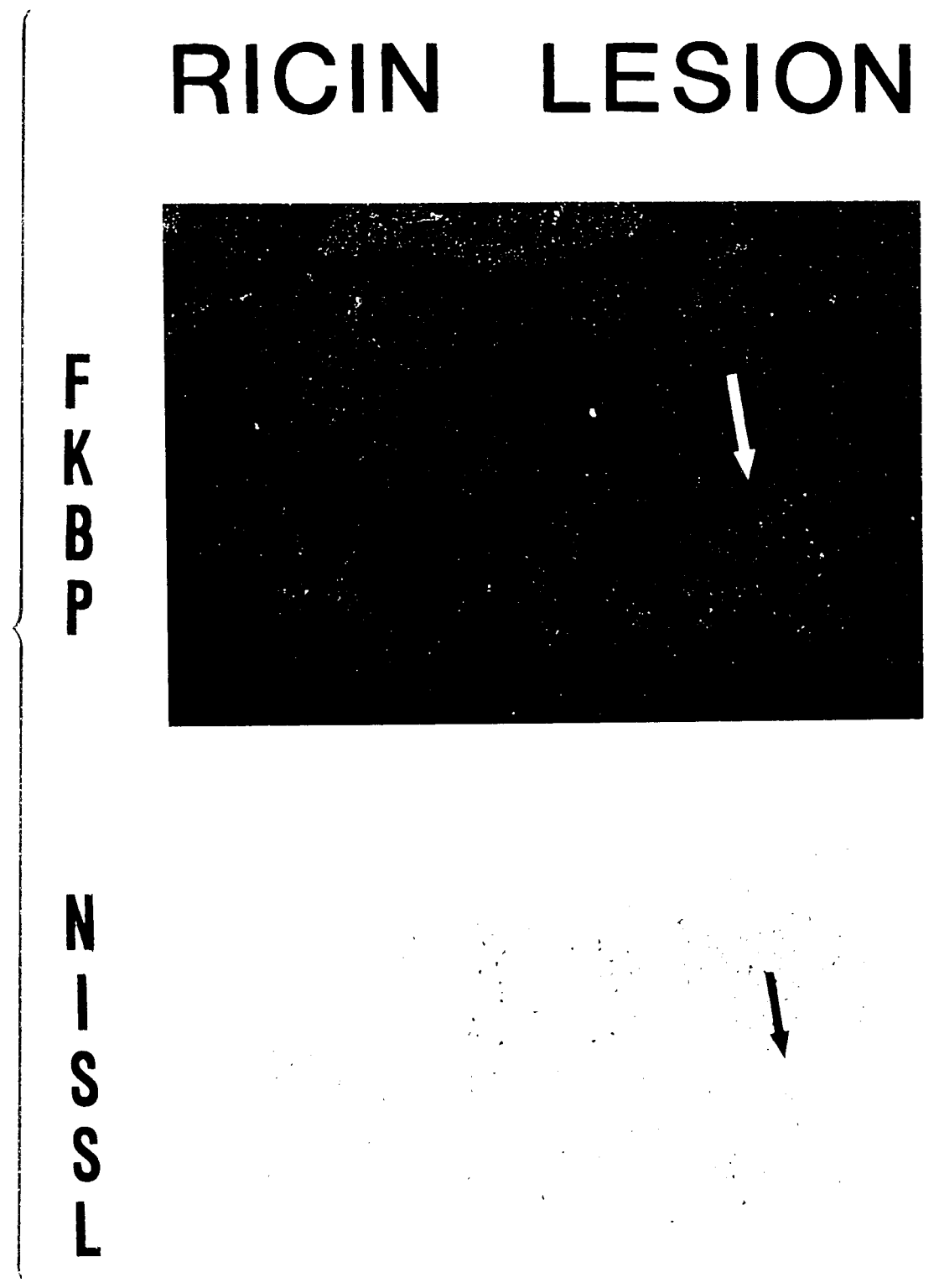

We conducted in situ hybridization localization studies for FKBP mRNA at 2, 4 and 7 days following ricin treatment (FIG. 5). No increase in FKBP mRNA is observed following ricin treatment. Gliosis occurs both following ricin treatment and nerve crush. The failure of FKBP mRNA to increase following ricin treatment fits with the selective neuronal localization of FKBP mRNA in the facial nucleus.

Example 4

This example demonstrates that FKBP is rapidly transported in the sciatic nerve.

Figure 6:
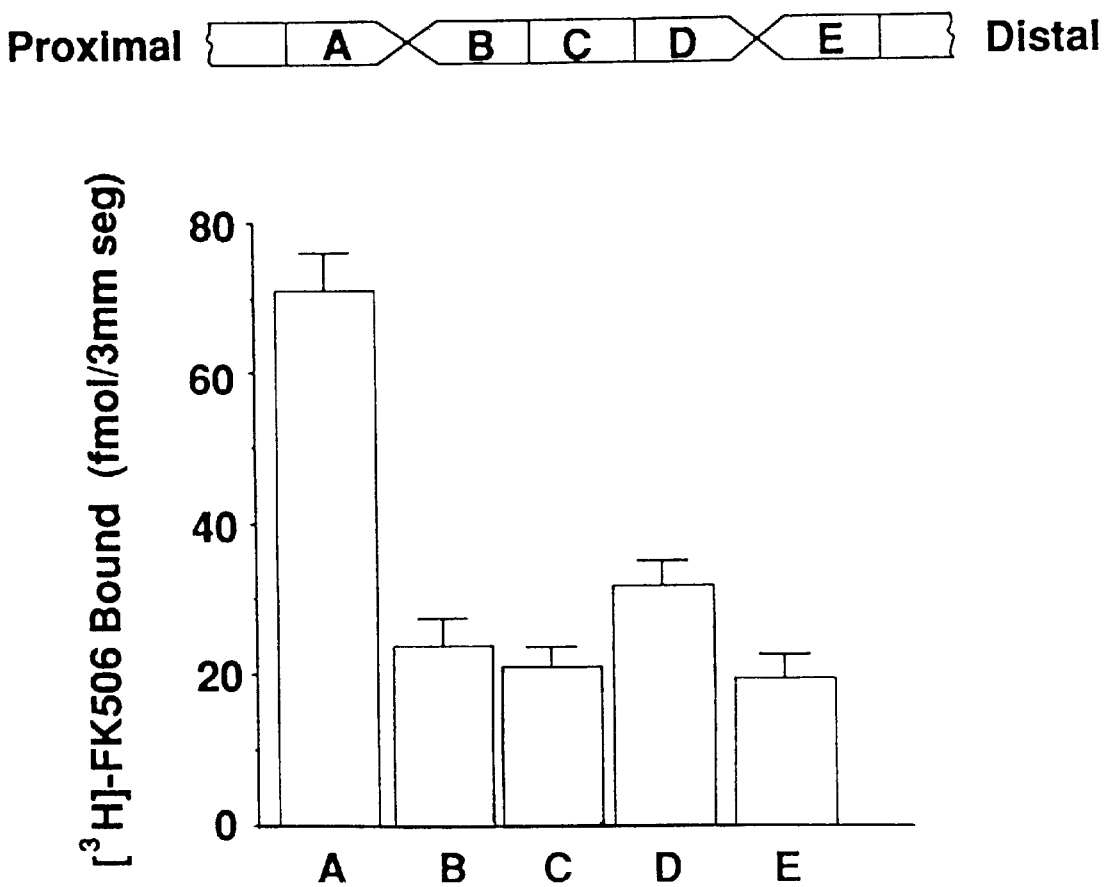

The failure of FKBP protein to increase in motor neurons following sciatic nerve crush despite the increase in FKBP mRNA suggests that the protein is rapidly transported out of the cell body into nerve processes. This fits with our earlier observations that FKBP mRNA is concentrated in granule cells of the cerebellum which contain low levels of FKBP protein, while FKBP protein levels are highly concentrated in the molecular layer in the cerebellum associated with the parallel fibers arising from granule cells (4). To examine for possible transport of FKBP, we crushed the sciatic nerve and 7 days later applied ligatures 10 and 20 mm proximal to the crush. Six hr following ligature, we monitored [$^3$H]FK-506 binding in 3 mm segments spanning the area of the ligatures. (FIG. 6).

For axon transport experiments, classic ligature techniques were used following the methods of Tetzlaff et al. One week following sciatic nerve crush two collection ligatures (510 sutures) were placed on the nerve approximately 10 mm apart with the distal most ligature positioned 10 mm proximal to the initial crush sight. Six hours later, 5-3 mm segments of the nerve were collected from regions proximal to, distal to, and between the collection ligatures as illustrated in FIG. 5. The nerve segments were prepared for [$^3$H]FK-506 binding assays by homogenizing in 10 volumes of 50 mM Tris-HCl, pH 7.4. Homogenates were centrifuged at 15,000 × g for 20 min at 4° C., and supernatants were collected and assayed for total protein concentration using the Coomassie blue dye binding assay (Pearce). [$^3$H]FK-506 binding was carried out as described (4) on aliquots containing 2 ug of total soluble protein in a final volume of 0.4 ml assay buffer consisting of 50 mM Tris-HCl, pH 7.4, 2 mg/ml bovine serum albumin, 250 pM [$^3$H]FK-506, and varying concentrations of unlabeled FK-506. Following incubation at 25° C. for 60 min, 0.35 ml was layered over a 0.8 ml column of LH-20 Sephadex (Pharmacia LKB) and washed with 0.4 ml of assay buffer. The eluates were collected and counted in a scintillation counter.

Results are shown in FIG. 5. [$^3$H]FKBP binding levels are highest in the segment just proximal to the ligature 20 cm from the crush, being almost quadruple levels in the other segments. Based on the levels of [$^3$H]FK-506 binding in segments A–D, we calculated the rate of anterograde transport for FKBP. This rate of 240 mm per day is essentially the same as transport rates for GAP-43 (18, 76, 77), representing the most rapid transport rates for neuronal proteins (78).

Figure 7:
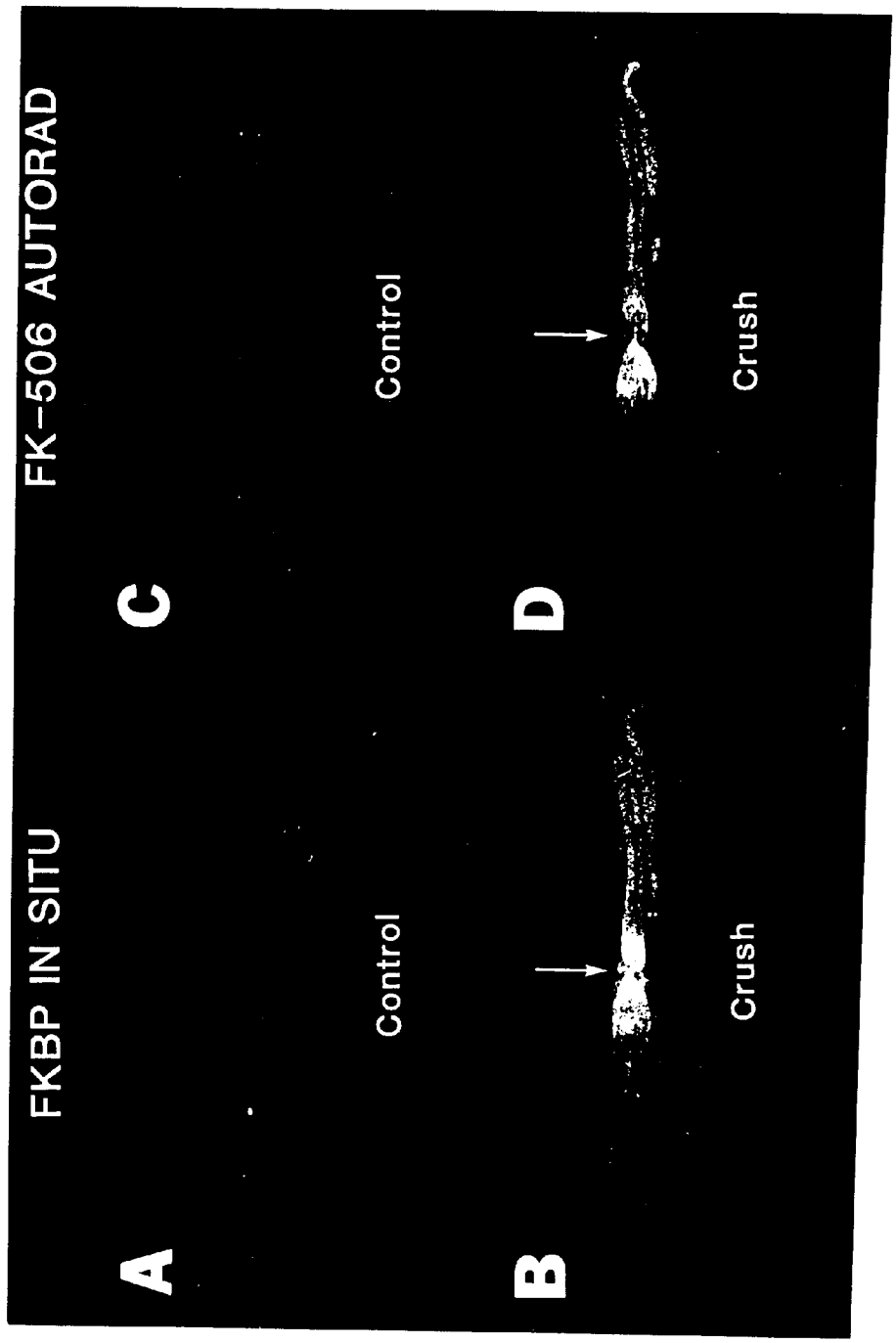

To visualize the accumulation of FKBP following nerve crush, we applied a loose ligature to mark the site of crush of the sciatic nerve and conducted in situ hybridization for FKBP mRNA as well autoradiography for [$^3$H]FK-506 binding (FIG. 7). Most FKBP mRNA and [$^3$H]FK-506 binding accumulate immediately proximal to the crush. These levels are considerably higher than in control uncrushed sciatic nerve. Examination of the in situ hybridization an autoradiography preparations at high magnification reveals silver grains associated with neuronal fibers. There are also silver grains localized to cells whose identity we could not determine definitively, so that they may be Schwann cells, macrophages or fibroblasts (data not shown).

Example 5

This example demonstrates that PC-12 cells contain FKBP and that FKBP levels are enhanced by nerve growth factor. We examined PC-12 cells for the presence of FKBP by monitoring the binding of [$^3$H]FK506 to cells under basal conditions and following treatment with nerve growth factor (NGF).

Levels of FKBP in PC-12 cells were obtained from Scatchard analysis of [$^3$H]FK506 binding curves. Cultures were scraped from the culture wells and homogenized in 10 volumes of 50 mM Tris-HCl, pH 7.4, 1 mM EDTA, 100 $\mu$g/ml phenylmethylsulfonylfluoride and centrifuged at 40,000 x g for 20 min at 4° C. Protein was determined by the Coomassie blue dye binding assay using bovine serum albumin as a standard. Binding of 250 pM [$^3$H]dihydro FK506 (86.5 Ci/mmol, DuPont/NEN) was assessed for samples containing 5 $\mu$g soluble protein in a final volume of 0.4 ml assay buffer containing 50 mM Tris-HCl, pH 7.4, 2 mg/ml BSA and varying concentrations of unlabeled FK506. After 60 min incubation at 25° C., 0.35 ml was layered over a 0.8 ml column of LH-20 Sephadex (Pharmacia LKB), pre-equilibrated with assay buffer. The column was further washed with 0.4 ml of assay buffer, the eluates collected, mixed with Formula 963 (DuPont/NEN) and counted in a Beckman scintillation counter. Specific binding was determined by subtracting binding obtained in the presence of 1 $\mu$M unlabeled FK506 from total [$^3$H]FK506 bound.

Figure 8:
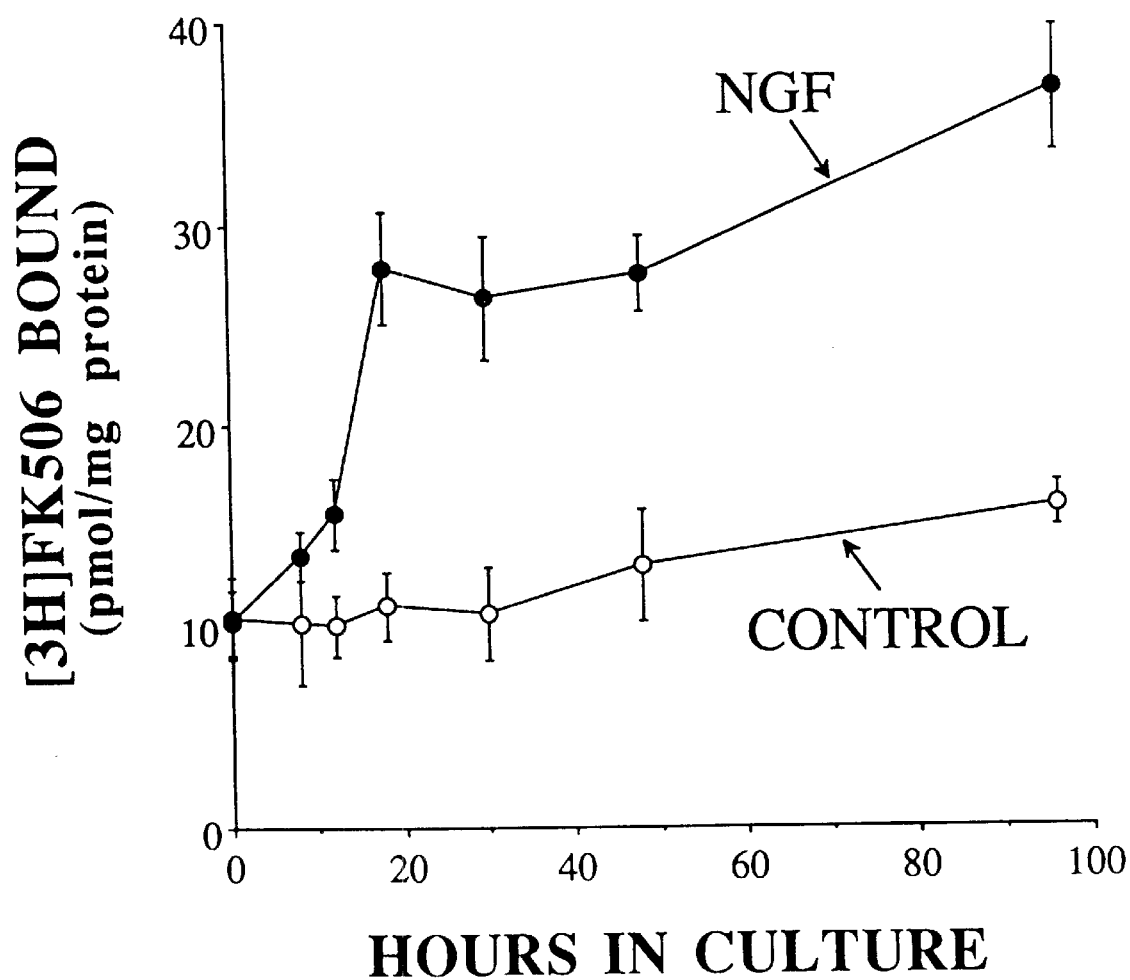

Results are shown in FIG. 8. [$^3$H]FK506 binds saturably to untreated PC-12 cell homogenates. In typical experiments about 1,000 cpm are bound while nonspecific binding in the presence of 1 $\mu$M FK506 is about 150 cpm. Fifty percent inhibition of [$^3$H]FK506 binding occurs with 1–2 nM FK506 indicating that the binding sites correspond to authentic FKBP. [$^3$H]FK506 binding increases markedly following NGF treatment. Significant increases are evident by 10–15 hr. Binding triples by 20 hr and a modest further increase is evident at 100 hr.

Example 6

This example demonstrates that FK506 and rapamycin increase neurite extension in PC-12 cells.

PC-12 cells were maintained at 37° C., 5% CO$_2$, in Dulbecco's modified Eagle medium (DMEM) supplemented with 10% heat-inactivated horse serum and 5% heat-inactivated fetal bovine serum. For differentiation in NGF, cells were plated at 1×10$^5$ in 35 mm culture wells coated with rat tail collagen at 5 $\mu$g/cm$^2$, and allowed to attach before replacing the media with DMEM supplemented with 2% fetal horse serum, 1% fetal calf serum, NGF and/or FK506 of rapamycin. For quantitation of neurite outgrowth, random photographs were made (3–4 per well), and process bearing neurons were counted with processes being greater than 5 $\mu$m. Experimental conditions were unknown by the photographer and cell counter. Four separate experiments were performed in duplicate for each data point presented. Neurites were identified and counted from approximately 100 cells per photograph. Thus, neurites from 1200–1600 cells were counted per data point.

Figure 10:
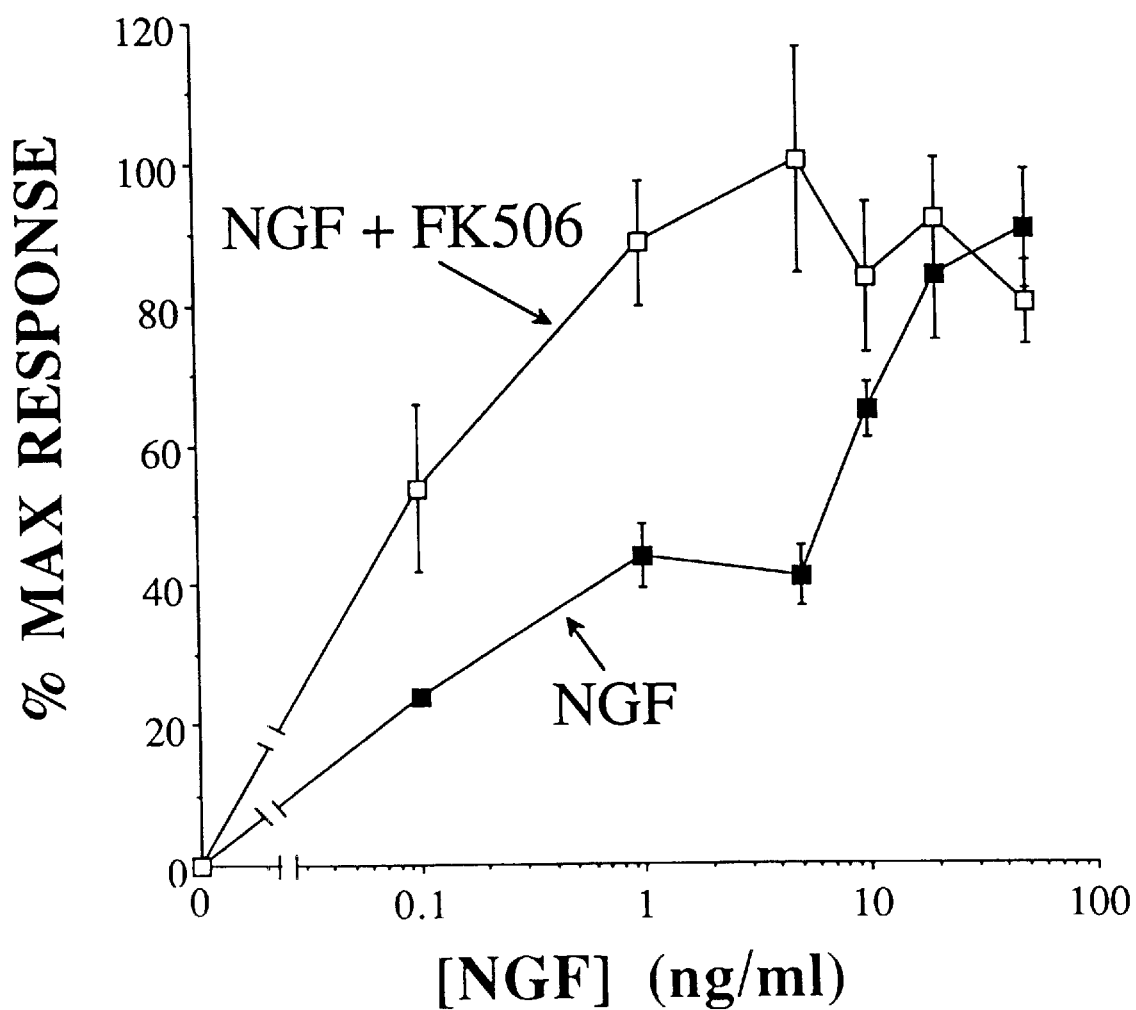

As observed by other workers (19,20), NGF potently stimulates neurite outgrowth with half-maximal stimulation at 1 ng/ml and maximal augmentation at about 50–100 ng/ml (FIGS. 9, 10). FK506 (100 nM) markedly augments the effect of NGF by increasing sensitivity to NGF. Thus, FK506 reduces by 20–50 fold the NGF concentration needed to elicit maximal outgrowth. Half maximal outgrowth in the absence of FK506 occurs at 5 ng/ml NGF and in the presence of FK506 at 0.1 ng/ml NGF. At maximal concentrations of NGF (10–100 ng/ml), FK506 fails to produce additional neurite outgrowth.

Figure 11:
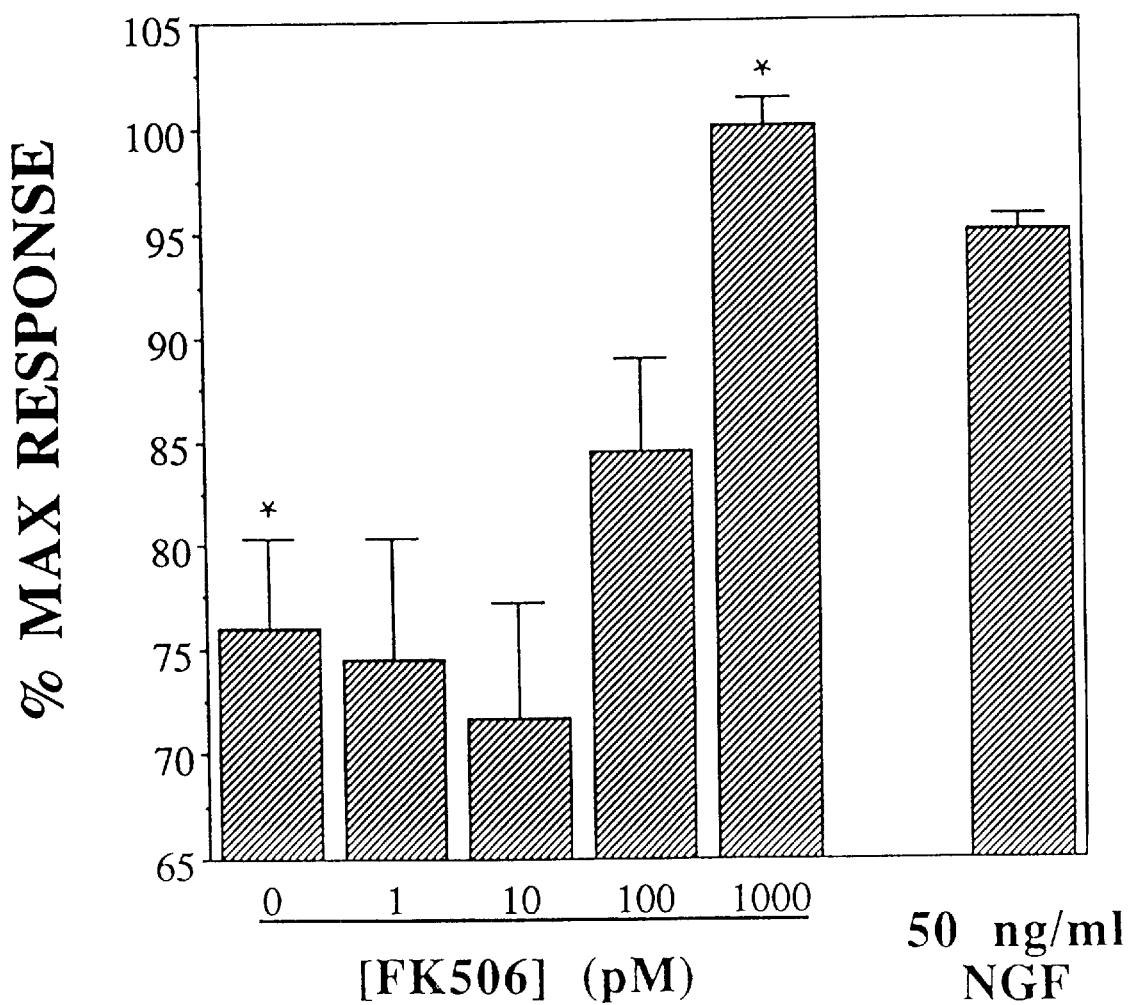

FK506 is extremely potent in its neurotrophic effects. In the presence of a submaximal concentration of NGF (1 ng/ml) FK506 at 1 nM elicits the same maximal outgrowth observed with 50 ng/ml NGF. (FIG. 11). Half maximal effects of FK506 occur at approximately 100 pM. In the absence of NGF, FK506 fails to elicit neurite outgrowth (FIG. 10).

Rapamycin is a potent immunosuppressant which is not thought to act through calcineurin but which may influence other phosphorylation cascades (21–28). Rapamycin potently blocks actions of FK506 that occur through FKBP and calcineurin presumably by acting as an FK506 antagonist at FKBP (7,21,29,30). Rapamycin (1 $\mu$M) fails to block the neurotrophic actions of FK506 (data not shown). Instead, rapamycin is itself neurotrophic providing major neurite outgrowth at 1 nM. Rapamycin and FK506 seem to be acting via different mechanisms. Thus, rapamycin augments the number of processes as well as their length, while FK506 primarily increases neurite length. Moreover, effects of FK506 and rapamycin appear to be additive (data not shown).

Example 7

This example demonstrates that FK506 is neurotrophic for sensory ganglia. We examined the action of FK506 on primary cultures of dorsal root ganglia from rats at embryonic day 16.

Stage E16 embryos were removed from pregnant Sprague-Dawley rats and the dorsal root ganglia dissected. Whole ganglia explants were cultured in collagen-coated 35 mm dishes (Falcon) using N2 medium (Dulbecco's Modified Eagle medium and Ham's F12 medium mixed 1:1 and supplemented with progesterone, selenium, insulin, putrescine, glucose, and penicillin-streptomycin) at 37° C. in a 15% CO$_2$ environment. Sensory ganglia were treated with various concentrations of NGF and/or FK506 or rapamycin or anti-NGF antibody. Ganglia were observed every 2–3 days under phase-contrasting using an Olympus IMT-2 inverted microscope, and measurements of axon length were made. The axonal field of each ganglion was divided into four quadrants, and the length of the longest axons in each quadrant was measured in microns using an eye-piece micrometer. The average of these measurements was taken as the axon length for the ganglion.

For [$^3$H]FK506 autoradiography, dorsal root ganglia cultures were grown on chamber slides coated with collagen, 5 $\mu$g/cm$^2$. Cultures were fixed on the slide with ice cold 4.0% freshly depolymerized paraformaldehyde in 0.1 M sodium phosphate buffer, pH 7.4, for 1 hr, then washed two times with phosphate buffered saline. Fixed cultures were labeled with [$^3$H]FK506 by pre-incubating the slides in a buffer consisting of 50 mM Hepes, 2 mg/ml bovine serum albumin, 0.02% Tween-20 pH 7.4. This was followed by incubation in the same assay buffer containing 1 nM [$^3$H]FK506. Non-specific binding was determined by adding 1 μM unlabeled FK506. The slides were then rinsed 4× 5 min prior to drying, and juxtaposed to tritium-sensitive film for 10 days.

Figure 12:

Autoradiography of [$^3$H]FK506 binding sites reveals substantial levels of FKBP associated silver grains in these ganglia (FIG. 12). At 1 μM unlabeled FK506, autoradiographic grains are abolished indicating the specificity of binding. As reported previously (31), NGF (100 ng/ml) markedly increases the number and length of ganglia processes (FIG. 13). FK506 (1 μM) alone produces a similar neurotrophic effect, while as little as 1 nM FK506 produces a noticeable increase in growth. Rapamycin (1 μM) which acts as an FK506 antagonist, completely blocks the effects of FK506 (1 μM), thus the action of FK506 displays a drug specificity characteristic of FKBP (3,9,10,32).

Whereas FK506 fails to stimulate neurite outgrowth in PC-12 cells in the absence of added NGF, in sensory ganglia FK506 alone is neurotrophic. Schwann cells in the ganglia can fabricate NGF, and the production of NGF by Schwann cells is regulated by a protein phosphorylation event (33). To ascertain whether the actions of FK506 alone involve potentiation of endogenous NGF, we examined the influence of antibodies to NGF (FIG. 13). Anti-NGF markedly reduces the neurotrophic effects of FK506 (1 μM). The anti-NGF is not acting in a toxic fashion as we observe no morphologic evidence of toxicity in the cells exposed to anti-NGF in the presence or absence of added NGF.

FK506 is extremely potent in stimulating neurite outgrowth. As little as 1 pM FK506 produces detectable augmentation. Progressively greater outgrowth occurs at 0.1 and 10 nM FK506 (data not shown), while maximal outgrowth requires 1 μM FK506.

The time course of neurite outgrowth is similar at all concentrations of NGF and FK506. Some outgrowth is evident by 1 day, while growth begins to plateau at about 5–6 days.

FK506 neurotrophic effects involve FKBP (FK506 binding protein) in sensory ganglia since the effects of FK506 are reversed by low concentrations of rapamycin, a known antagonist of FK506 at FKBP (7,21,29,30). The failure of rapamycin to block FK506 effects in PC-12 cells probably reflects the separate stimulatory effects of rapamycin. Mechanisms for rapamycin stimulation of neurite outgrowth in PC-12 cells are not immediately evident. Its immunosuppressant actions are thought to involve different mechanisms than those of FK506. Rapamycin can inhibit S6 kinase which phosphorylates the S6 ribosomal subunit (22–24,26, 28). Rapamycin also inhibits phosphatidylinositol-3-kinase (25).

Protein kinase C (PKC)—mediated phosphorylation has been implicated in process outgrowth during neuronal regeneration (36–40). Other evidence suggests inhibitory effects of PKC in neuronal process extension (41–44).

GAP43 is a prominent calcineurin substrate highly concentrated in neurites (14) and its phosphorylation is regulated by FKBP (4). GAP43 may not be directly involved in neurite extension, as PC-12 cell lines with low levels of GAP43 display normal neurite outgrowth (45). However, GAP43 and its phosphorylation may be involved in targeting neurites, as levels of phosphorylated GAP43 are increased when neurites approach their targets (46). Phosphorylation of GAP-43 may also influence mobilization of $Ca^{2+}$ that regulates neurite extension. Phosphorylated GAP-43 inhibits phosphatidyl inositol bis-phosphate formation, which should diminish levels of inositol 1,4,5-triphosphate and associated $Ca^{2+}$ release (17). In addition, phosphorylation of GAP-43 decreases its affinity for calmodulin with the resultant free calmodulin available to bind $Ca^{2+}$ (17).

Immunophilins may act at sites besides calcineurin which affect $Ca^{2+}$ that regulates neurite outgrowth. FKBP binds to the ryanodine receptor, which is a $Ca^{2+}$ release channel (47). In skeletal muscle sarcoplasmic reticulum FK506 dissociates FKBP from the ryanodine receptor to facilitate the $Ca^{2+}$ induced $Ca^{2+}$ release mechanism (48). In addition, FK506 acts at other sites including FKBP25 (49,50), steroid receptors (51,52) and other unidentified targets such as those related to FKBP13 (53). Thus other potential mechanisms may play some role in neurite extension.

References

1. Handschumacher, R. E., Harding, M. W., Rice, J., Drugge, R. J. & Speicer, D. W. (1984) Science 226, 544–547.

2. Swanson, S. K. -H., Born, T., Zydowsky, L. D., Cho, H., Chang, H. Y., Walsh, C. T. & Rusnak, F. (1992) Proc. Natl. Acad. Sci. USA 89, 3741–3745.

3. McKeon, F. (1991) Cell 66, 823–826.

4. Steiner, J. P., Dawson, T. M., Fotuhi, M., Glatt, C. E., Snowman, A. M., Cohen, N. & Snyder, S. H. (1992) Nature 358, 584–587.

5. Liu, J., Farmer, J. D., Jr., Lane, W. S., Friedman, J., Weissman, I. & Schreiber, S. L. (1991) Cell 66, 807–815.

6. Liu, J., Albers, M. W., Wandless, T. J., Luan, S., Alberg, D. G., Belshaw, P. J., Cohen, P., MacKintosh, C., Klee, C. B. & Schreiber, S. L. (1992) Biochemistry 31, 3896–3901.

7. Dumont, F. J., Melino, M. R., Staruch, M. J., Koprak, S. L., Fisher, P. A. & Sigal, N. H. (1990) J. Immunol. 144, 1418–1424.

8. Fruman, D. A., Klee, C. B., Bierer, B. E. & Burakoff, S. J. (1992) Proc. Natl. Acad. Sci. USA 89, 3686–3690.

9. Schreiber, S. L. & Crabtree, G. R. (1992) Immunology Today 13, 136–142.

10. Dawson, T. M., Steiner, J. P., Dawson, V. L., Dinerman, J. L., Uhl, G. R. & Snyder, S. H. (1993) Proc. Natl. Acad. Sci. USA 90, 9808–9812.

11. Bredt, D. S., Ferris, C. D. & Snyder, S. H. (1992) J. Biol. Chem. 267, 10976–10981.

12. Dawson, V. L., Dawson, T. M., London, E. D., Bredt, D. S. & Snyder, S. H. (1991) Proc. Natl. Acad. Sci. USA 88, 6368–6371.

13. Dawson, V. L., Dawson, T. M., Bartley, D. A., Uhl, G. R. & Snyder, S. H. (1993) J. Neurosci. 13, 2651–2661.

14. Liu, Y. & Storm, D. R. (1989) J. Biol. Chem. 264, 12800–12804.

15. Snipes, G. J., Costello, B., McGuire, C. B., Mayes, B. N., Bock, S. S., Norden, J. J. & Freeman, J. A. (1987) Prog. in Brain Res. 71, 155–175.

16. Benowitz, L. I. & Routtenberg, A. (1987) Trends Neurosci. 10, 527–532.

17. Skene, J. H. P. (1989) Ann. Rev. Neurosci. 12, 127–156.

18. Tetzlaff, W., Zwiers, H., Lederis, K., Cassar, L. & Bisby, M. A. (1989) J. Neurosci. 9, 1303–1313.

19. Greene, L. A. & Tischler, A. S. (1976) *Proc. Natl. Acad. Sci. USA* 73, 2424–2428.

20. Yanker, B. A., Benowitz, L. I., Villa-Komaroff, L. & Neve, R. L. (1990) *Mol. Brain. Res.* 71, 39–44.

21. Bierer, B. E., Mattila, P. S., Standaert, R. F., Herzenberg, L. A., Burakoff, S. J., Crabtree, G. & Schreiber, S. L. (1990) *Proc. Natl. Acad. Sci. USA* 87, 9231–9235.

22. Calvo, V., Crews, C. M., Vik, T. A. & Bierer, B. E. (1992) *Proc. Natl. Acad. Sci. USA* 89, 7571–7575.

23. Chung, J., Kuo, C. J., Crabtree, G. R. & Blenis, J. (1992) *Cell* 69, 1227–1236.

24. Kuo, C. J., Chung, J., Fiorentino, D. F., Flanagan, W. M., Blenis, J. & Crabtree, G. R. (1992) *Nature* 358, 70–73.

25. Kunz, J., Henriquez, R., Schneider, U., Deuter-Reinhard, M., Movva, N. R. & Hall, M. N. (1993) *Cell* 73, 585–596.

26. Price, D. J., Grove, J. R., Calvo, V., Avruch, J. & Bierer, B. E. (1993) *Science* 257, 973–977.

27. Jin, Y. J. & Burakoff, S. J. (1993) *Proc. Natl. Acad. Sci. USA* 90, 7769–7773.

28. Ferrari, S., Pearson, R. B., Siegman, M., Kozma, S. C. & Thomas, G. (1993) *J. Biol. Chem.* 268, 16091–16094.

29. Schreiber, S. L. (1991) *Science* 253, 283–287.

30. Dumont, F. J., Staruch, M. J., Koprak, S. L., Melino, M. R. & Sigal, N. H. (1990) *J. Immunol.* 144, 251–258.

31. Thoenen, H. & Barde, Y. A. (1980) *Physiol. Rev.* 60.4, 1284–1335.

32. DeFranco, A. L. (1991) *Nature* 352, 754–755.

33. Matsuoka, I., Meyer, M. & Thoenen, H. (1991) *J. Neurosci.* 11.10, 3165–3177.

34. Levi, A., Biocca, A., Cattaneo, A. & Calissano, P. (1988) *Molec. Neurobio.* 2, 201–226.

35. Fujita, K., Lazarovici, P. & Guroff, G. (1989) *Environ. Health Prosp.* 80, 127–142.

36. Mechta, S., Hsu, L., Jeng, A. Y. & Chen, K. Y. (1993) *J. Neurochem.* 60, 972–981.

37. Hsu, L. (1988) *Anat. Embryol.* 179, 511–578.

38. Hall, F. L., Fernyhough, P., Ishir, D. N. & Vulliet, P. R. (1988) *J. Biol. Chem.* 263, 4460–4466.

39. Hashimoto, S. & Hagine, A. (1989) *J. Neurochem.* 1675, 1685.

40. Bixby, J. L. (1989) *Neuron* 3, 287–297.

41. Morrison, R. S., Gross, J. L. & Moskal, J. R. (1988) *Brain Res.* 473, 141–146.

42. Mattson, M. P., Guthrie, P. B. & Kater, S. B. (1988) *J. Neurosci. Res.* 21, 447–464.

43. Girard, P. R. & Kuo, J. F. (1990) *J. Neurochem.* 54, 300–306.

44. Reinhold, D. S. & Nect, K. E. (1989) *J. Biol. Chem.* 102, 821–829.

45. Baetge, E. E. & Hammang, J. P. (1993) *Neuron* 6, 21–30.

46. Meiri, K. F., Bickerstaff, L. E. & Schwob, J. E. (1991) *J. Cell Biol.* 112, 991–1005.

47. Jayraman, T., Brillantes, A. M., Timerman, A. P., Fleischer, S., Erdjument-Bromage, H., Tempst, P. & Marks, A. (1992) *J. Biol. Chem.* 267, 9474–9477.

48. Timerman, A. P., Ogunbumni, E., Freund, E., Wiederrecht, G., Marks, A. R. & Fleischer, S. (1993) *J. Biol. Chem.* 268, 22992–22999.

49. Galat, A., Lane, W. S., Standaert, R. F. & Schreiber, S. L. (1992) *Biochemistry* 31, 2427–2434.

50. Jin, Y. J., Burakoff, S. J. & Bierer, B. E. (1992) *J. Biol. Chem.* 267, 10942–10945.

51. Tai, P. -K. K., Albers, M. W., Chang, H., Faber, L. E. & Schreiber, S. L. (1992) *Science* 256, 1315–1318.

52. Yem, A. W., Tomasselli, A. G., Heinrikson, R. L., Zurcher-Neely, H., Ruff, V. A., Johnson, R. A. & Deibel, M. R., Jr. (1992) *J. Biol. Chem.* 267, 2868–2871.

53. Jin, Y. -J., Albers, M. W., Lane, W. S., Bierer, B. E., Schreiber, S. L. & Burakoff, S. J. (1991) *Proc. Natl. Acad. Sci. USA* 88, 6677–6681.

54. Phelps, C. H., Gage, F. H., Growden, J. H., Hefti, F., Harbaugh, R., Johnson, M. V., Khachaturian, Z. S. & Mobley, W. C. (1989) *Neurobio. Aging* 10, 205–207.

55. Tetzlaff, W., et al. (1991) *J. Neurosci.* 11, 2528–2544.

56. Maki, N., et al. (1990) *Proc. Natl. Acad. Sci. USA* 87, 5440–5443.

57. Standaert, R. F., et al. (1990) *Nature* 346, 671–674.

58. Rosenthal, A., et al. (1987) *EMBO J.* 6, 3641–3646.

59. Ito, A., et al. (1989) *Biochem. Biophys. Res. Commun.* 163, 1492–1497.

60. Kuno, T., et al. (1989) *Biochem. Biophys. Res. Commun.* 165, 1352–1358.

61. Lieberman, A. R. (1971) *Int. Rev. Neurobiol.* 14, 49–124.

62. Saika, T., et al. (1991) *Mol. Brain. Res.* 9, 157–160.

63. Bisby, M. A. (1988) *Brain Res.* 458, 157–161.

64. Hoffman, P. N. (1989) *J. Neurosci.* 9, 893–897.

65. Sommervaille, T., et al. (1991) *Neuroscience* 45, 213–220.

66. Van der Zee, C. E. E. M., et al. (1989) *J. Neurosci.* 9, 3505–3512.

67. Verge, V. M. K., et al. (1990) *J. Neurosci.* 10, 926–934.

68. Wiese, U. H., et al. (1991) *Res. Neurol. Neurosci.* 10, 2215–2222.

69. Schreyer, D. J., et al. (1991) *J. Neurosci.* 11, 3738–3751.

70. Woolf, C. J., et al. (1990) *Neuroscience* 34, 465–478.

71. Chong, M. S., et al. (1992) *Eur. J. Neurosci.* 4, 883–895.

72. Basi, G. S., et al. (1987) *Cell* 49, 785–791.

73. Wiese, U. H., et al. (1992) *Brain Res.* 592, 141–156.

74. Wiley, R. G., et al. (1982) *Science* 216, 889–890.

75. Streit, W. J., et al. (1988) *J. Comp. Neurol.* 268, 248–263.

76. Skene, J. H. P., et al. (1981a) *J. Cell Biol.* 89, 86–95.

77. Skene, J. H. P., et al. (1981b) *J. Cell Biol.* 89, 96–103.

78. Grafstein, B., et al. (1980) *Physiol. Rev.* 60, 1167–1282.

We claim:

1. A method of stimulating growth of damaged peripheral nerves, comprising:
    administering to damaged peripheral nerves an immunophilin ligand and a neurotrophic factor in amounts sufficient to stimulate the growth of said nerves.

2. The method of claim 1 wherein the immunophilin ligand is FK506.

3. The method of claim 1 wherein the immunophilin ligand is rapamycin.

4. The method of claim 1 wherein the immunophilin ligand is cyclosporin A.

5. The method of claim 1 wherein the neurotrophic factor is NGF (nerve growth factor).

6. The method of claim 1 wherein the neurotrophic factor is GDNF (glial derived growth factor).

7. The method of claim 1 wherein the neurotrophic factor is BDNF (brain derived growth factor).

8. The method of claim 1 wherein the neurotrophic factor is CNTF (ciliary neurotrophic factor).

9. The method of claim 1 wherein the neurotrophic factor is neurotropin-3.

10. A method of stimulating growth of damaged neurons in the spinal cord, comprising:

administering to damaged neurons in the spinal cord an immunophilin ligand and a neurotrophic factor in amounts sufficient to stimulate growth of said neuronal cells.

11. The method of claim 10 wherein the neurotrophic factor is NGF (nerve growth factor).

12. The method of claim 10 wherein the neurotrophic factor is GDNF (glial derived growth factor).

13. The method of claim 10 wherein the neurotrophic factor is BDNF (brain derived growth factor).

14. The method of claim 10 wherein the neurotrophic factor is CNTF (ciliary neurotrophic factor).

15. The method of claim 10 wherein the neurotrophic factor is neurotropin-3.

16. The method of claim 10 wherein the immunophilin ligand is FK506.

17. The method of claim 10 wherein the immunophilin ligand is rapamycin.

18. The method of claim 10 wherein the immunophilin ligand is cyclosporin A.

19. A method of stimulating growth of motor neurons, comprising:

administering to motor neurons an immunophilin ligand and a neurotrophic factor in amounts sufficient to stimulate growth of said neuronal cells.

20. The method of claim 19 wherein the motor neurons are in a patient with amyotrophic lateral sclerosis.

21. A method of stimulating growth of damaged neurons, comprising:

administering to damaged neurons of a neurodegenerative disease patient an immunophilin ligand and a neurotrophic factor in amounts sufficient to stimulate growth of said damaged neurons.

22. The method of claim 1 wherein said immunophilin ligand binds to FKBP.

23. The method of claim 10 wherein said immunophilin ligand binds to FKBP.

24. The method of claim 19 wherein said immunophilin ligand binds to FKBP.

25. The method of claim 21 wherein said immunophilin ligand binds to FKBP.

26. The method of claim 1 wherein said immunophilin ligand does not bind to cyclophilin.

27. The method of claim 10 wherein said immunophilin ligand does not bind to cyclophilin.

28. The method of claim 19 wherein said immunophilin ligand does not bind to cyclophilin.

29. The method of claim 21 wherein said immunophilin ligand does not bind to cyclophilin.

* * * * *

UNITED STATES PATENT AND TRADEMARK OFFICE
CERTIFICATE OF CORRECTION

PATENT NO. : 5,898,029

DATED : April 27, 1999

INVENTOR(S) : LYONS, GEORGE, DAWSON, STEINER, SNYDER

Page 1 of 2

It is certified that error appears in the above-indentified patent and that said Letters Patent is hereby corrected as shown below:

Column 3, Line 46 please replace "µM" with -- pM --.
Column 2, Line 8 please replace "FIGS. 1A and 1B" with -- FIG. 1--.
Column 2, Line 19 please replace "FIGS. 2A and 2B" with -- FIG. 2--.
Column 2, Line 25 please replace "FIGS. 3A-3C" with -- FIG. 3--
Column 2, Line 64 please replace "FIGS. 7A-7D" with -- FIG. 7--
Column 3, Line 41 please replace "FIGS. 13A-13F" with -- FIG. 13--.

UNITED STATES PATENT AND TRADEMARK OFFICE
CERTIFICATE OF CORRECTION

PATENT NO. : 5,898,029
DATED : April 27, 1999
INVENTOR(S) : LYONS, GEORGE, DAWSON, STEINER, SNYDER It is certified that error appears in the above-indentified patent and that said Letters Patent is hereby corrected as shown below:

Column 9, Line 6 please replace "well autoradiography" with -- well as autoradiography --.

Column 9, Line 11 please replace "an" with -- and --.

Signed and Sealed this

Twenty-ninth Day of August, 2000

Attest:

Attesting Officer

Q. TODD DICKINSON

Director of Patents and Trademarks